(12) United States Patent
Fournie-Zaluski et al.

(10) Patent No.: US 7,875,436 B2
(45) Date of Patent: Jan. 25, 2011

(54) PEPTIDE SUBSTRATES RECOGNIZABLE BY A BOTULINUM TOXIN A, BONT/A AND THE USE THEREOF

(75) Inventors: Marie-Claude Fournie-Zaluski, Paris (FR); Bernard Pierre Roques, Paris (FR)

(73) Assignee: Pharmaleads, Paris (FR)

( * ) Notice: Subject to any disclaimer, the term of this patent is extended or adjusted under 35 U.S.C. 154(b) by 998 days.

(21) Appl. No.: 11/579,491

(22) PCT Filed: May 4, 2005

(86) PCT No.: PCT/FR2005/001121
§ 371 (c)(1), (2), (4) Date: Dec. 28, 2006

(87) PCT Pub. No.: WO2005/121354
PCT Pub. Date: Dec. 22, 2005

(65) Prior Publication Data
US 2009/0208993 A1 Aug. 20, 2009

(30) Foreign Application Priority Data

| May 5, 2004 | (FR) | 04 04817 |
| Feb. 11, 2005 | (FR) | 05 01435 |

(51) Int. Cl.
| C12Q 1/37 | (2006.01) |
| A61K 38/00 | (2006.01) |
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |

(52) U.S. Cl. .............. 435/24; 514/13; 514/14; 514/15; 514/16; 530/326; 530/328; 530/329; 530/330

(58) Field of Classification Search .............. None
See application file for complete search history.

(56) References Cited

U.S. PATENT DOCUMENTS 7,160,982 B2 * 1/2007 Roques et al. .............. 530/300

FOREIGN PATENT DOCUMENTS

| FR | 2 809 733 | 12/2001 |
| WO | WO 01/92312 | * 12/2001 |

OTHER PUBLICATIONS

Anne C et al: "High-Throughput Fluorogenic Assay for Determination of Botulinum Type B Neurotoxin Protease Activity" Analytical Biochemistry, Academic Press, New York, NY, US, vol. 291, No. 2, Apr. 15, 2001, pp. 253-261, XP001023970 ISSN: 0003-2697 abstract, p. 254, col. 1, paragraph 1.

Soleilhac et al: "A sensitive and rapid fluorescence-based assay for determination of tetanus toxin peptidase activity" Analytical Biochemistry, Academic Press, San Diego, CA, US, vol. 241, 1996, pp. 120-127, XP002160418 ISSN: 0003-2697 the whole document.

Luciani N et al: "Highly Sensitive and Selective Fluorescence Assays for Rapid Screening of Endothelin-Converting Enzyme Inhibitors" Biochemical Journal, The Biochemical Society, London, GB, vol. 356, No. 3, Jun. 15, 2001, pp. 813-819, XP001025608 ISSN: 0264-6021 the whole document.

* cited by examiner

*Primary Examiner*—Marcela M Cordero Garcia
(74) *Attorney, Agent, or Firm*—Young & Thompson

(57) ABSTRACT

A peptide substrate selectively recognisable by a botulinum toxin A, BoNT/A containing a Nop-(Z)-Pya fragment in the peptide structure thereof, wherein Z is an aminoacid chain, preferably RA and the fragment is cleaved by the toxin.

14 Claims, 9 Drawing Sheets

Figures 2A, 2B:
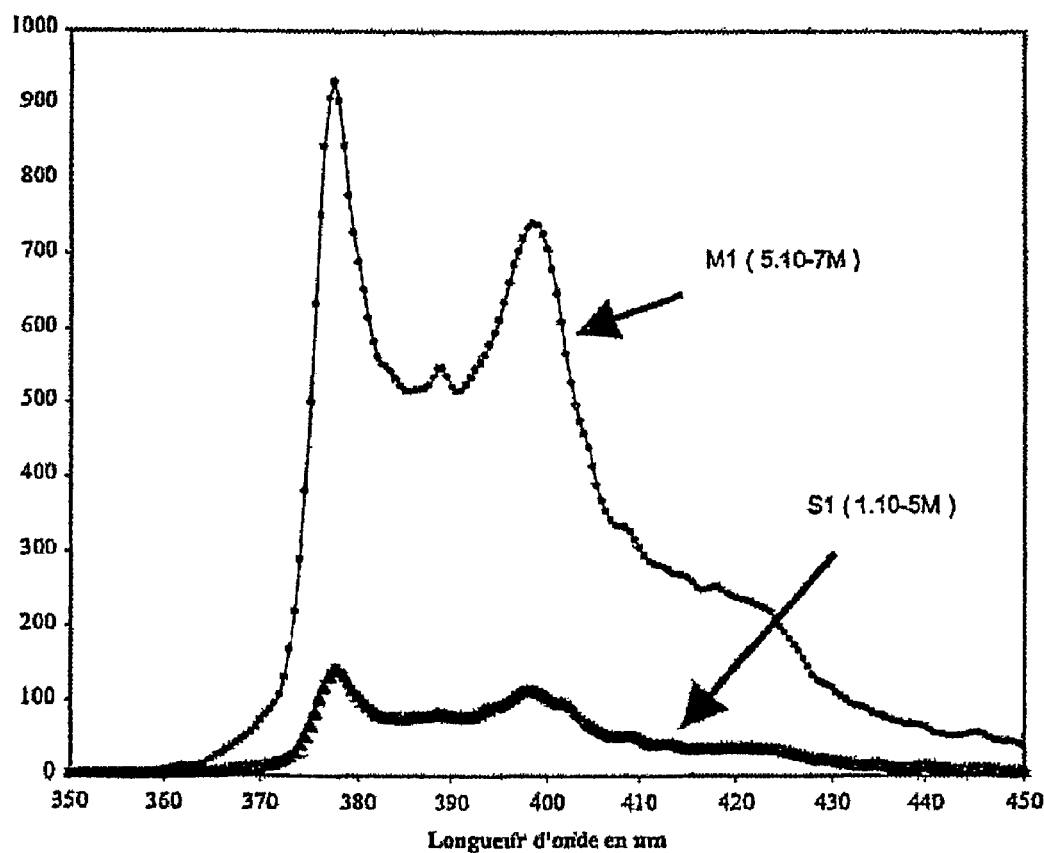

Dégradation des peptides 1 et 2 par la toxine botulique de type A mesurée à 37°C.
(Cytofluor λex=340 nm; λem=400 nm, Gain=76)

Figure 1

---Nop↓R-A-Pya---

Fluorescence du substrat S1 et son metabolite M1

Activité de la toxine botulique A en absence et en présence d'EDTA

Figure 4

Dégradation de S9(10μM) par différentes concentrations de BoNT/A (exprimée en DL50 souris, 1DL50=2pg)

Figure 5

Figure 8

S9 : Substrat à fluorescence réprimée pour la détection-quantification de la toxine botulique A (BoNT/A)

Structure :
Ac-Ile-Ile-Gly-Asn-Leu-Arg-His-Met-Ala-Leu-Asp-Met-Gly-Asn-Glu-Ile-Asp-Thr-Gln-Asn-Arg-Gln-Ile-Asp-Arg-Ile-Met-Glu-Lys-Ala-Asp-Ser-Asn-Lys-Thr-Arg-Ile-Asp-Glu-Ala-Asn-(pNO$_2$Phe)-Arg-Ala-PyrenylAla-Lys-Nle-Leu-NH$_2$ Synthèse : Synthèse en phase solide chimie Fmoc.

Poids Moléculaire :
6739.7 (8 TFA en contre-ions)

Analyse acides aminés :

| | | |
|---|---|---|
| Asx : 9.76/10 | Thr : 1.91/2 | Cys : X |
| Glx : 5.03/5 | Ala : 4.17/4 | Ile: 5.14/6 |
| Ser: 1 ;00/1 | Pro: X | Leu: 4.20/3 |
| Gly : 1.97/2 | Tyr : X | Phe : X |
| His : 0.96/1 | Val: X | Trp: X |
| Arg: 5.07/5 | Met: 2.58/3 | Lys: 3.14/3 | pNO$_2$-Phe a été détecté mais non quantifié. Nle coélue avec Leu. Il y a une hydrolyse incomplète entre Ile-Ile. Met est partiellement détruit lors de l'hydrolyse.

HPLC:
Colonne Kromasil C18 Gradient 10% CH$_3$CN à 90% CH$_3$CN/10% H$_2$0 (0.5% TFA) en 30 min, $\lambda$= 343 nm ; Rt= 15.96 min.

Représentation de Michaelis Menten avec PL50 et BoNT/A

$K_m = 3.98\ \mu M$
$k_{cat} = 2.79\ s^{-1}$
$k_{cat}/K_m = 7.01 \cdot 10^5\ M^{-1} \cdot s^{-1}$ Vitesse de clivage (pmol / min / µg) vs Concentration PL50 (µM)

Inset: Vitesse (pmol / min / µg) vs (vitesse / concentration de substrat) pmol / min / µg d'enzyme / µM de substrat

Figure 9

SEQUENCE LISTING

<160> NUMBER OF SEQ ID NOS: 27

<210> SEQ ID NO 1
<211> LENGTH: 206
<212> TYPE: PRT
<213> ORGANISM: Homo sapiens

<400> SEQUENCE: 1

Met Ala Glu Asp Ala Asp Met Arg Asn Glu Leu Glu Glu Met Gln Arg
1               5                   10                  15

Arg Ala Asp Gln Leu Ala Asp Glu Ser Leu Glu Ser Thr Arg Arg Met
            20                  25                  30

Leu Gln Leu Val Glu Glu Ser Lys Asp Ala Gly Ile Arg Thr Leu Val
        35                  40                  45

Met Leu Asp Glu Gln Gly Glu Gln Leu Glu Arg Ile Glu Glu Gly Met
    50                  55                  60

Asp Gln Ile Asn Lys Asp Met Lys Glu Ala Glu Lys Asn Leu Thr Asp
65                  70                  75                  80

Leu Gly Lys Phe Cys Gly Leu Cys Val Cys Pro Cys Asn Lys Leu Lys
                85                  90                  95

Ser Ser Asp Ala Tyr Lys Lys Ala Trp Gly Asn Asn Gln Asp Gly Val
            100                 105                 110

Val Ala Ser Gln Pro Ala Arg Val Val Asp Glu Arg Glu Gln Met Ala
        115                 120                 125

Ile Ser Gly Gly Phe Ile Arg Arg Val Thr Asn Asp Ala Arg Glu Asn
    130                 135                 140

Glu Met Asp Glu Asn Leu Glu Gln Val Ser Gly Ile Ile Gly Asn Leu
145                 150                 155                 160

Arg His Met Ala Leu Asp Met Gly Asn Glu Ile Asp Thr Gln Asn Arg

```
                         165                 170                 175
Gln Ile Asp Arg Ile Met Glu Lys Ala Asp Ser Asn Lys Thr Arg Ile
            180                 185                 190
Asp Glu Ala Asn Gln Arg Ala Thr Lys Met Leu Gly Ser Gly
        195                 200                 205

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Asn Lys Thr Arg Ile Asp Glu Ala Asn Gln Arg Ala Thr Lys Met
 1               5                  10                  15
Leu

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Nop
<220> FEATURE:
<221> NAME/KEY: MOD_RES
<222> LOCATION: (4)
<223> OTHER INFORMATION: Pya

<400> SEQUENCE: 3

Xaa Arg Ala Xaa
 1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Nop
<220> FEATURE:
<221> NAME/KEY: MOD_RES
<222> LOCATION: (5)
<223> OTHER INFORMATION: Pya

<400> SEQUENCE: 4

Xaa Arg Ala Thr Xaa
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
```

```
<223> OTHER INFORMATION: Nop
<220> FEATURE:
<221> NAME/KEY: MOD_RES
<222> LOCATION: (6)
<223> OTHER INFORMATION: Pya

<400> SEQUENCE: 5

Xaa Arg Ala Thr Lys Xaa
  1               5

<210> SEQ ID NO 6
<211> LENGTH: 72
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(52)
<223> OTHER INFORMATION: Variable amino acid and this region may
      encompass 0 or 2-52 residues
<220> FEATURE:
<221> NAME/KEY: MOD_RES
<222> LOCATION: (60)
<223> OTHER INFORMATION: Glu or Gln
<220> FEATURE:
<221> NAME/KEY: MOD_RES
<222> LOCATION: (63)
<223> OTHER INFORMATION: Nop
<220> FEATURE:
<221> NAME/KEY: MOD_RES
<222> LOCATION: (66)
<223> OTHER INFORMATION: Pya
<220> FEATURE:
<221> NAME/KEY: MOD_RES
<222> LOCATION: (68)
<223> OTHER INFORMATION: Nle
<220> FEATURE:
<221> NAME/KEY: MOD_RES
<222> LOCATION: (69)
<223> OTHER INFORMATION: May or may not be present
<220> FEATURE:
<221> NAME/KEY: MOD_RES
<222> LOCATION: (70)..(72)
<223> OTHER INFORMATION: Region may or may not be present
<220> FEATURE:
<223> OTHER INFORMATION: See specification as filed for detailed
      description of substitutions and preferred embodiments

<400> SEQUENCE: 6

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa
         35                  40                  45

Xaa Xaa Xaa Xaa Ser Asn Lys Thr Arg Ile Asp Xaa Ala Asn Xaa Arg
     50                  55                  60

Ala Xaa Lys Xaa Leu Gly Ser Gly
 65                  70

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
```

```
<220> FEATURE:
<221> NAME/KEY: MOD_RES
<222> LOCATION: (1)
<223> OTHER INFORMATION: Asp, Cys or not present
<220> FEATURE:
<221> NAME/KEY: MOD_RES
<222> LOCATION: (9)
<223> OTHER INFORMATION: Glu or Gln
<220> FEATURE:
<221> NAME/KEY: MOD_RES
<222> LOCATION: (12)
<223> OTHER INFORMATION: Nop
<220> FEATURE:
<221> NAME/KEY: MOD_RES
<222> LOCATION: (15)
<223> OTHER INFORMATION: Pya
<220> FEATURE:
<221> NAME/KEY: MOD_RES
<222> LOCATION: (17)
<223> OTHER INFORMATION: Nle
<220> FEATURE:
<221> NAME/KEY: MOD_RES
<222> LOCATION: (18)
<223> OTHER INFORMATION: May or may not be present
<220> FEATURE:
<223> OTHER INFORMATION: C-term amidated
<220> FEATURE:
<223> OTHER INFORMATION: See specification as filed for detailed
      description of substitutions and preferred embodiments

<400> SEQUENCE: 7

Xaa Ser Asn Lys Thr Arg Ile Asp Xaa Ala Asn Xaa Arg Ala Xaa Lys
 1               5                  10                  15

Xaa Leu

<210> SEQ ID NO 8
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (11)
<223> OTHER INFORMATION: Nop
<220> FEATURE:
<221> NAME/KEY: MOD_RES
<222> LOCATION: (14)
<223> OTHER INFORMATION: Pya
<220> FEATURE:
<221> NAME/KEY: MOD_RES
<222> LOCATION: (16)
<223> OTHER INFORMATION: Nle
<220> FEATURE:
<223> OTHER INFORMATION: C-term amidated

<400> SEQUENCE: 8

Ser Asn Lys Thr Arg Ile Asp Glu Ala Asn Xaa Arg Ala Xaa Lys Xaa
 1               5                  10                  15

Leu

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
```

```
<220> FEATURE:
<221> NAME/KEY: MOD_RES
<222> LOCATION: (12)
<223> OTHER INFORMATION: Nop
<220> FEATURE:
<221> NAME/KEY: MOD_RES
<222> LOCATION: (15)
<223> OTHER INFORMATION: Pya
<220> FEATURE:
<221> NAME/KEY: MOD_RES
<222> LOCATION: (17)
<223> OTHER INFORMATION: Nle
<220> FEATURE:
<223> OTHER INFORMATION: C-term amidated

<400> SEQUENCE: 9

Cys Ser Asn Lys Thr Arg Ile Asp Glu Ala Asn Xaa Arg Ala Xaa Lys
 1               5                  10                  15

Xaa Leu

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (11)
<223> OTHER INFORMATION: Nop
<220> FEATURE:
<221> NAME/KEY: MOD_RES
<222> LOCATION: (14)
<223> OTHER INFORMATION: Pya
<220> FEATURE:
<221> NAME/KEY: MOD_RES
<222> LOCATION: (16)
<223> OTHER INFORMATION: Nle
<220> FEATURE:
<223> OTHER INFORMATION: C-term amidated

<400> SEQUENCE: 10

Ser Asn Lys Thr Arg Ile Asp Gln Ala Asn Xaa Arg Ala Xaa Lys Xaa
 1               5                  10                  15

Leu

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)
<223> OTHER INFORMATION: Nop
<220> FEATURE:
<221> NAME/KEY: MOD_RES
<222> LOCATION: (15)
<223> OTHER INFORMATION: Pya
<220> FEATURE:
<221> NAME/KEY: MOD_RES
<222> LOCATION: (17)
<223> OTHER INFORMATION: Nle
<220> FEATURE:
<223> OTHER INFORMATION: C-term amidated
```

```
<400> SEQUENCE: 11

Cys Ser Asn Lys Thr Arg Ile Asp Gln Ala Asn Xaa Arg Ala Xaa Lys
  1               5                   10                  15

Xaa Leu

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (11)
<223> OTHER INFORMATION: Nop
<220> FEATURE:
<221> NAME/KEY: MOD_RES
<222> LOCATION: (14)
<223> OTHER INFORMATION: Pya
<220> FEATURE:
<221> NAME/KEY: MOD_RES
<222> LOCATION: (16)
<223> OTHER INFORMATION: Nle
<220> FEATURE:
<223> OTHER INFORMATION: C-term amidated

<400> SEQUENCE: 12

Ser Asn Lys Thr Arg Ile Asp Gln Ala Asn Xaa Arg Ala Xaa Lys Xaa
  1               5                   10                  15

<210> SEQ ID NO 13
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (12)
<223> OTHER INFORMATION: Nop
<220> FEATURE:
<221> NAME/KEY: MOD_RES
<222> LOCATION: (15)
<223> OTHER INFORMATION: Pya
<220> FEATURE:
<221> NAME/KEY: MOD_RES
<222> LOCATION: (17)
<223> OTHER INFORMATION: Nle
<220> FEATURE:
<223> OTHER INFORMATION: C-term amidated

<400> SEQUENCE: 13

Cys Ser Asn Lys Thr Arg Ile Asp Gln Ala Asn Xaa Arg Ala Xaa Lys
  1               5                   10                  15

Xaa

<210> SEQ ID NO 14
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
```

```
<220> FEATURE:
<221> NAME/KEY: MOD_RES
<222> LOCATION: (14)
<223> OTHER INFORMATION: Nop
<220> FEATURE:
<221> NAME/KEY: MOD_RES
<222> LOCATION: (17)
<223> OTHER INFORMATION: Pya
<220> FEATURE:
<221> NAME/KEY: MOD_RES
<222> LOCATION: (19)
<223> OTHER INFORMATION: Nle
<220> FEATURE:
<223> OTHER INFORMATION: C-term amidated

<400> SEQUENCE: 14

Lys Ser Asp Ser Asn Lys Thr Arg Ile Asp Glu Ala Asn Xaa Arg Ala
 1               5                  10                  15

Xaa Lys Xaa Leu Gly Ser Gly
            20

<210> SEQ ID NO 15
<211> LENGTH: 52
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: Met or Nle
<220> FEATURE:
<221> NAME/KEY: MOD_RES
<222> LOCATION: (29)
<223> OTHER INFORMATION: Met or Nle
<220> FEATURE:
<221> NAME/KEY: MOD_RES
<222> LOCATION: (33)
<223> OTHER INFORMATION: Met or Nle
<220> FEATURE:
<221> NAME/KEY: MOD_RES
<222> LOCATION: (48)
<223> OTHER INFORMATION: Met or Nle

<400> SEQUENCE: 15

Arg Arg Val Thr Asn Asp Ala Arg Glu Asn Glu Xaa Asp Glu Asn Leu
 1               5                  10                  15

Glu Gln Val Ser Gly Ile Ile Gly Asn Leu Arg His Xaa Ala Leu Asp
            20                  25                  30

Xaa Gly Asn Glu Ile Asp Thr Gln Asn Arg Gln Ile Asp Arg Ile Xaa
        35                  40                  45

Glu Lys Ala Asp
    50

<210> SEQ ID NO 16
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)
<223> OTHER INFORMATION: Met or Nle
<220> FEATURE:
<221> NAME/KEY: MOD_RES
<222> LOCATION: (23)
<223> OTHER INFORMATION: Met or Nle
<220> FEATURE:
```

```
<221> NAME/KEY: MOD_RES
<222> LOCATION: (27)
<223> OTHER INFORMATION: Met or Nle
<220> FEATURE:
<221> NAME/KEY: MOD_RES
<222> LOCATION: (42)
<223> OTHER INFORMATION: Met or Nle

<400> SEQUENCE: 16

Ala Arg Glu Asn Glu Xaa Asp Glu Asn Leu Glu Gln Val Ser Gly Ile
 1               5                  10                  15

Ile Gly Asn Leu Arg His Xaa Ala Leu Asp Xaa Gly Asn Glu Ile Asp
            20                  25                  30

Thr Gln Asn Arg Gln Ile Asp Arg Ile Xaa Glu Lys Ala Asp
        35                  40                  45

<210> SEQ ID NO 17
<211> LENGTH: 41
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Met or Nle
<220> FEATURE:
<221> NAME/KEY: MOD_RES
<222> LOCATION: (18)
<223> OTHER INFORMATION: Met or Nle
<220> FEATURE:
<221> NAME/KEY: MOD_RES
<222> LOCATION: (22)
<223> OTHER INFORMATION: Met or Nle
<220> FEATURE:
<221> NAME/KEY: MOD_RES
<222> LOCATION: (37)
<223> OTHER INFORMATION: Met or Nle

<400> SEQUENCE: 17

Xaa Asp Glu Asn Leu Glu Gln Val Ser Gly Ile Ile Gly Asn Leu Arg
 1               5                  10                  15

His Xaa Ala Leu Asp Xaa Gly Asn Glu Ile Asp Thr Gln Asn Arg Gln
            20                  25                  30

Ile Asp Arg Ile Xaa Glu Lys Ala Asp
        35                  40

<210> SEQ ID NO 18
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Met or Nle
<220> FEATURE:
<221> NAME/KEY: MOD_RES
<222> LOCATION: (12)
<223> OTHER INFORMATION: Met or Nle
<220> FEATURE:
<221> NAME/KEY: MOD_RES
<222> LOCATION: (27)
<223> OTHER INFORMATION: Met or Nle

<400> SEQUENCE: 18

Ile Ile Gly Asn Leu Arg His Xaa Ala Leu Asp Xaa Gly Asn Glu Ile
```

```
                1               5              10              15

Asp Thr Gln Asn Arg Gln Ile Asp Arg Ile Xaa Glu Lys Ala Asp
               20              25              30

<210> SEQ ID NO 19
<211> LENGTH: 69
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (63)
<223> OTHER INFORMATION: Nop
<220> FEATURE:
<221> NAME/KEY: MOD_RES
<222> LOCATION: (66)
<223> OTHER INFORMATION: Pya
<220> FEATURE:
<221> NAME/KEY: MOD_RES
<222> LOCATION: (68)
<223> OTHER INFORMATION: Nle
<220> FEATURE:
<223> OTHER INFORMATION: C-term amidated

<400> SEQUENCE: 19

Arg Arg Val Thr Asn Asp Ala Arg Glu Asn Glu Met Asp Glu Asn Leu
 1               5              10              15

Glu Gln Val Ser Gly Ile Ile Gly Asn Leu Arg His Met Ala Leu Asp
               20              25              30

Met Gly Asn Glu Ile Asp Thr Gln Asn Arg Gln Ile Asp Arg Ile Met
        35              40              45

Glu Lys Ala Asp Ser Asn Lys Thr Arg Ile Asp Glu Ala Asn Xaa Arg
     50              55              60

Ala Xaa Lys Xaa Leu
 65

<210> SEQ ID NO 20
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (42)
<223> OTHER INFORMATION: Nop
<220> FEATURE:
<221> NAME/KEY: MOD_RES
<222> LOCATION: (45)
<223> OTHER INFORMATION: Pya
<220> FEATURE:
<221> NAME/KEY: MOD_RES
<222> LOCATION: (47)
<223> OTHER INFORMATION: Nle
<220> FEATURE:
<223> OTHER INFORMATION: C-term amidated

<400> SEQUENCE: 20

Ile Ile Gly Asn Leu Arg His Met Ala Leu Asp Met Gly Asn Glu Ile
 1               5              10              15

Asp Thr Gln Asn Arg Gln Ile Asp Arg Ile Met Glu Lys Ala Asp Ser
               20              25              30
```

Asn Lys Thr Arg Ile Asp Glu Ala Asn Xaa Arg Ala Xaa Lys Xaa Leu
            35                  40                  45

<210> SEQ ID NO 21
<211> LENGTH: 48
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (8)
<223> OTHER INFORMATION: Nle
<220> FEATURE:
<221> NAME/KEY: MOD_RES
<222> LOCATION: (12)
<223> OTHER INFORMATION: Nle
<220> FEATURE:
<221> NAME/KEY: MOD_RES
<222> LOCATION: (27)
<223> OTHER INFORMATION: Nle
<220> FEATURE:
<221> NAME/KEY: MOD_RES
<222> LOCATION: (42)
<223> OTHER INFORMATION: Nop
<220> FEATURE:
<221> NAME/KEY: MOD_RES
<222> LOCATION: (45)
<223> OTHER INFORMATION: Pya
<220> FEATURE:
<221> NAME/KEY: MOD_RES
<222> LOCATION: (47)
<223> OTHER INFORMATION: Nle
<220> FEATURE:
<223> OTHER INFORMATION: C-term amidated

<400> SEQUENCE: 21

Ile Ile Gly Asn Leu Arg His Xaa Ala Leu Asp Xaa Gly Asn Glu Ile
 1               5                  10                  15

Asp Thr Gln Asn Arg Gln Ile Asp Arg Ile Xaa Glu Lys Ala Asp Ser
            20                  25                  30

Asn Lys Thr Arg Ile Asp Glu Ala Asn Xaa Arg Ala Xaa Lys Xaa Leu
            35                  40                  45

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pya
<220> FEATURE:
<221> NAME/KEY: MOD_RES
<222> LOCATION: (5)
<223> OTHER INFORMATION: Nle
<220> FEATURE:
<221> NAME/KEY: MOD_RES
<222> LOCATION: (6)
<223> OTHER INFORMATION: May or may not be present
<220> FEATURE:
<221> NAME/KEY: MOD_RES
<222> LOCATION: (7)..(9)
<223> OTHER INFORMATION: Region may or may not be present
<220> FEATURE:
<223> OTHER INFORMATION: C-term amidated

```
<400> SEQUENCE: 22

Arg Ala Xaa Lys Xaa Leu Gly Ser Gly
 1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pya
<220> FEATURE:
<221> NAME/KEY: MOD_RES
<222> LOCATION: (5)
<223> OTHER INFORMATION: Nle
<220> FEATURE:
<223> OTHER INFORMATION: C-term amidated

<400> SEQUENCE: 23

Arg Ala Xaa Lys Xaa Leu
 1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pya
<220> FEATURE:
<221> NAME/KEY: MOD_RES
<222> LOCATION: (5)
<223> OTHER INFORMATION: Nle
<220> FEATURE:
<223> OTHER INFORMATION: C-term amidated

<400> SEQUENCE: 24

Arg Ala Xaa Lys Xaa
 1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Pya
<220> FEATURE:
<221> NAME/KEY: MOD_RES
<222> LOCATION: (5)
<223> OTHER INFORMATION: Nle
<220> FEATURE:
<223> OTHER INFORMATION: C-term amidated

<400> SEQUENCE: 25

Arg Ala Xaa Lys Xaa Leu Gly Ser Gly
 1               5

<210> SEQ ID NO 26
```

```
<211> LENGTH: 42
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (42)
<223> OTHER INFORMATION: Nop

<400> SEQUENCE: 26

Ile Ile Gly Asn Leu Arg His Met Ala Leu Asp Met Gly Asn Glu Ile
 1               5                  10                  15

Asp Thr Gln Asn Arg Gln Ile Asp Arg Ile Met Glu Lys Ala Asp Ser
            20                  25                  30

Asn Lys Thr Arg Ile Asp Glu Ala Asn Xaa
        35                  40

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<221> NAME/KEY: MOD_RES
<222> LOCATION: (11)
<223> OTHER INFORMATION: Pya
<220> FEATURE:
<221> NAME/KEY: MOD_RES
<222> LOCATION: (14)
<223> OTHER INFORMATION: Nop
<220> FEATURE:
<221> NAME/KEY: MOD_RES
<222> LOCATION: (16)
<223> OTHER INFORMATION: Nle
<220> FEATURE:
<223> OTHER INFORMATION: C-term amidated

<400> SEQUENCE: 27

Ser Asn Lys Thr Arg Ile Asp Glu Ala Asn Xaa Arg Ala Xaa Lys Xaa
 1               5                  10                  15

Leu
```

PEPTIDE SUBSTRATES RECOGNIZABLE BY A BOTULINUM TOXIN A, BONT/A AND THE USE THEREOF

The present invention relates to peptide substrates selectively recognized by botulinum toxin type A, BoNT/A, and their uses, in particular for carrying out methods for detecting, identifying and/or dosing botulinum toxin type A, or inhibitors and/or activators of the metallopeptidase activity of said toxin.

The neurotoxin type A (BoNT/A) forms part of a family of seven related proteins (botulinum toxins A to G) produced by different strains of the anaerobic bacillus "clostridium botulinum". The two forms which are the most frequently encountered and the most dangerous are the type A and B toxins. The LD50 lethal doses in mice by intraperitoneal route are 2 pg for toxin A and approximately 50 to 100 pg for toxin B. They act at the level of the peripheral nervous system in humans and various animal species by inducing "botulism" characterized by flaccid paralysis of the skeletal muscles which can result in death.

The major form of intoxication by these toxins is due to the ingestion of contaminated food or drink. But these toxins can also constitute a potential biological weapon to the extent that they are easy to produce. On the other hand, for several years, the botulinum toxins, and more particularly BoNT/A, have been used for therapeutic (dystonia, neuronal hyperactivity such as strabismus, blepharospasm etc.) or aesthetic applications (in particular wrinkle reduction). For all these applications, it is essential to have a simple, quick and sensitive method for the detection and quantification of botulinum toxin type A in various media, including biological media.

The botulinum neurotoxins are constituted by two protein sub-units: a heavy chain (100 kD) linked to a light chain (50 kD) via a disulphide bridge. The heavy chain is involved in the binding of the toxin to the nerve ending, in the internalization then in the translocation of the light chain into the cytosol. The light chain is responsible for the toxicity of the protein by inhibition of the calcium-dependent release of acetylcholine.

The toxicity of the light chain of these toxins is due to its peptidase activity. In fact, the botulinum toxins belong to the family of zinc metallopeptidases and more particularly to the sub-family of the zincins which contain the consensus sequence HExxH; (Schiavo et al. (1992) J. Biol. Chem. 267, 23479-23483; Roques B. P. (1993) Biochem. Soc. Trans. 21, 678-685).

They cleave very specifically the neuronal proteins involved in the exocytosis of the neurotransmitters, such as SNAP 25 and synaptobrevin. The cleavage site is specific to each toxin, including to an identical substrate.

Botulinum toxin type A cleaves specifically one of the SNARE complex proteins, SNAP-25 (sequence SEQ ID NO: 1). This protein of 206 amino acids is cleaved specifically at the level of the Q197-R198 bond.

Previous works have shown that fragments shorter than this SNAP 25 sequence (1-206) could also be degraded by BoNT/A (Schmidt and Bostian, J. Prot. Chem., 1997, 16, 19-26). This is the case with the minimum SNAP 25 (187-203) fragment: $^{187}$S N K T R I D E A N Q R A T K M L$^{203}$ (sequence SEQ ID NO: 2).

The most effective approach for combatting the harmful effects of BoNT/A, either in the course of a declared case of botulism, or in the course of therapeutic counter-indications, is the development of inhibitors which are selective and have a high affinity for its metallopeptidase activity, which is responsible for its toxicity. However, the identification of such inhibitors, and the determination of their effectiveness (inhibition constants, Ki), require a simple BoNT/A activity measurement test which can be automated, allowing a large number of tests (HTS).

The tests currently available are not satisfactory for such applications.

On the other hand, the most sensitive method for detecting the botulinum toxins is an in vivo test which is based on the determination of the median lethal dose (LD50) in mice (Kautter and Salomon (1976) J. Assoc. Anal. Chem., 60, 541-545). Although very sensitive, since it makes it possible to detect 5 to 10 pg of BoNT/A, this method has numerous drawbacks: the response time is several days and it does not appear to be the most precise method for estimating the biological activity of a therapeutic toxin preparation (Pearce et al. (1994) Tox. Applied Pharmacol., 128, 69-77). Moreover, the estimation of the LD50 varies very widely with the toxin preparation, the mouse strain, etc. Finally it should be noted that animal experimentation is becoming more and more controversial.

Tests on cell lines have been proposed (De Waart et al. (1972) Zentralblatt für Bacteriologie, 222, 96-114), but their sensitivity is insufficient (1000 mouse LD50). Immunological tests have been developed [radioimmunoassays (Boroff and Shu-Chen, 1973, Applied Microbiol., 25, 545-549), ELISA tests (Hallis et al., 1993 in Botulinum and Tetanus Toxins DasGupta B. R. editor, New York: Plenum Press) with amplification systems (Stanley et al., 1985, J. Immunol. and Methods, 83, 89-95)], but none is sufficiently sensitive. Moreover, they produce a significant proportion of false positives.

A few tests, based on the peptidase activity of BoNT/A have been developed. On the one hand, study of the cleavage of SNAP 25 or its SNAP 25 (137-206) fragment (Hallis et al. (1996) J. Clinic. Microbiol., 34, 1934-1938) immobilized on resin, followed by detection of the metabolite fixed on the resin by an antibody, then an amplification system, has led to the demonstration of approximately 1000 mouse LD50/ml. Nevertheless this method is time-consuming and expensive.

The characterization by Schmidt and Bostian (J. Prot. Chem. (1997), 16, 19-26) of the smallest fragment of SNAP 25 recognized by BoNT/A, (187-203) SNAP 25, has led to the demonstration of the first fluorigenic substrate of BoNT/A by introduction of a dnp (dinitrophenyl) group and DACIA (dim-

```
SEQ ID NO: 1: ¹M A E D A D M R N E L E E M Q R R A D Q L A D E S L E S

T R R M L Q L V E E S K D A G I R T L V M L D E Q G E Q L E R I E E G M D Q I

N K D M K E A E K N L T D L G K F C G L C V C P C N K L K S S D A Y K K A W

G N N Q D G V V A S Q P A R V V D E R E Q M A I S G G F I R R V T N D A R E

N E M D E N L E Q V S G I I G N L R H M A L D M G N E I D T Q N R Q I D R I M

E K A D S N K T R I D E A N Q¹⁹⁷ --¹⁹⁸R A T K M L G S G²⁰⁶
``` ethyl-amino-coumarinyl) on the side chains of a lysine at position 197 and a cysteine at position 200, respectively (Schmidt and Stafford, Applied Environ. Microbiol. (2003), 69, 297-303). This method allows rapid detection of quantities greater than or equal to 100 ng/ml.

Nevertheless, not all these methods have the sensitivity, reproducibility, reliability and ease of use required for detecting and quantifying doses of native BoNT/A less than or equal to 1 ng/ml, the concentration corresponding to the lethal dose for a man weighing 70 kg being of the order of 1 µg. This involves detecting doses of less than 5 ng in a small volume of medium infected by BoNT/A, in case of ingestion.

The precise subject of the present invention is to propose a novel test for the detection and quantification of BoNT/A in response to these requirements.

The method chosen for the BoNT/A assay within the framework of the present invention is based on the phenomenon of fluorescence extinction by collision between a fluorophore (L.pyrenyl-alanine, Pya) and a very polar element (L.p-nitro-phenylalanine, NOP) (substrate with fluorescence repressed according to a mechanism of repression by collision; patent FR 0004507). Unlike FRET (fluorescence resonance energy transfer), there is no recovery of the fluorescence emission spectrum of the L-Pya residue and the L-NOP absorption spectrum. Pyrenylalanine Pya has very significant fluorescence which is virtually totally extinguished when Pya is placed in a peptide chain in proximity to the Nop residue. Consequently, the fluorescence of Pya can only be manifested from the moment when the peptide sequence situated between Pya and Nop is cleaved.

The extinction of fluorescence of Pya in the presence of NOP is due to the establishment during excitation by irradiation of a novel excited state different from that of Pya in the absence of NOP. The novel state is deactivated very easily and rapidly by internal conversion of the energy, without emission (non-radiative method).

The method chosen within the framework of the present invention is therefore very clearly distinguished from that used in FRET. In the latter case, as indicated previously, the recovery of the acceptor (quencher) absorption spectrum and donor (fluorophore) emission spectrum creates a novel excited state different from that created in the absence of the acceptor. This state is very easily deactivated by internal energy conversion, without emission (non-radiative method). The theoretical aspect of these methods is reported in: Yaron et al., Anal. Biochem. 95, 228-235 (1979) and Lakowicz J. R., Principles of fluorescence spectroscopy, $2^{nd}$ ed., Ed. KA.PP.

In the two methods, the fluorescence extinction is dependent on the distance between the two fluorophores. The effectiveness of the two methods can be studied experimentally on precise examples where the configurations (distances between the two partners) are optimum. This is the case with the following molecules into which the entities involved have been introduced side by side.

FRET

DABCYL-CO-↑-NH-EDANS

DABCYL=4-[4(dimethylaminopenyl-azo)benzoic acid]
EDANS=Ethylene-DiAmino-Naphthalene-Sulphonate.

The enzymatic hydrolysis of the CONH bond theoretically disperses the two partners DABCYL and EDANS ad infinitum. The observed increase in fluorescence of EDANS in this case is of the order of 200 UA (arbitrary unit) [G. T. Wang et al., Tet. Lett. 31, (1990)].

Collision Complex

Pya-CO-↑-NH-Nop

The increase in fluorescence of Pya during the enzymatic cleavage of the peptide bond CONH leads to an enhancement of fluorescence of 800 UA. [N. Luciani et al., Biochem. J. 356 (2001); patent Fr 00.04507, PCT/FR01/01058].

This better enhancement of fluorescence observed with the use of the Pya/Nop collision complex, is at the origin of the inventors' choice of the Pya-Nop or Nop-Pya couples, and not FRET.

The inventors have previously described a substrate very specific to the botulinum toxin type B, into which Pya and Nop residues have been introduced at positions 74 and 77 respectively of the 60-94 fragment of synaptobrevin, the minimum natural substrate of BoNT/B (patent FR 0007113; C. Anne et al. Analytical Biochem. (2001), 291, 253-261).

In the case of BoNT/A, the natural substrate is SNAP 25, and the minimum sequence of SNAP 25 cleaved by BoNT/A is the SNAP 25 (187-203) fragment (Schmidt and Bostian, above) corresponding to the formula SNAP25 (187-203)=$^{187}$S-N-K-T-R-I-D-E-A-N-Q$^{197}$R-A-T-K-M-L$^{203}$ (SEQ ID NO: 2) indicated above.

The cleavage of this peptide, or of the natural peptide substrate SNAP25, by BoNT/A, is carried out at the level of the $Q^{197}$-$R^{198}$ bond.

In the same manner as was carried out in the case of the assay of the BoNT/B with a fragment of synaptobrevin, the inventors introduced on both sides of the cleavage site of SNAP25 by botulinum toxin type A, a Pya residue at position 195, 196 or 197, and a Nop residue at position 199, 200, or 201 of these different SNAP25 fragments.

Unexpectedly, these modifications have led to the formation of peptides which are not, or only in a few cases, BoNT/A substrates. Thus, only the peptide Pya$^{197}$Nop$^{200}$(187-203) SNAP25 is weakly cleaved by the toxin BoNT/A at a high concentration (200 ng/ml), with only a doubling of the basic fluorescence in approximately 1 hour (FIG. 1).

This result therefore suggests significant differences in the structure of the active site of the two botulinum toxins A and B as well as in their mode of action.

On the other hand, surprisingly, the replacement of the Pya-(Z)-Nop sequence by the reversed sequence Nop-(Z)-Pya, with Z representing an amino acids chain chosen in such a manner that this reversed sequence can be cleaved by BoNT/A, made it possible to obtain excellent BoNT/A substrates, the sensitivity of which is up to 100 times greater than that of the substrates cleaved by BoNT/A and containing the Pya-(Z)-Nop sequence.

The present invention is therefore based on the fact that it is possible to detect an intense fluorescence caused by the separation of the Nop and Pya residues integrated into a BoNT/A substrate during enzymatic cleavage by this neurotoxin of one of the bonds situated between these residues, providing that the Nop residue is situated in the N-terminal metabolite and the Pya residue is situated in the C-terminal metabolite. FIG. 2a illustrates this phenomenon.

Thus, the main aim of the present invention is to provide a peptide substrate recognized by BoNT/A, which can be used within the framework of the implementation of methods for detecting, identifying and/or assaying type A botulinum toxin at very low concentrations (of the order of 20 pg), or inhibitors and/or activators of the metallopeptidase activity of said toxin, and in the latter case for quantifying their power.

A first aspect of the invention therefore relates to a peptide substrate, selectively recognized by BoNT/A toxin, characterized in that it comprises in its peptide structure an Nop-(Z)-Pya fragment in which Z represents an amino acids chain, said fragment being cleaved by said toxin.

Advantageously Z represents from 2 to 4 amino acids chosen such that the above-mentioned Nop-(Z)-Pya fragment is cleaved by BoNT/A.

Advantageously, in order to preserve the specificity and effectiveness of BoNT/A, the amino acids of the substrates of the invention are chosen from those of the natural SNAP25 sequence.

Advantageously also, Z contains the residues arginine R at position 198 and A at position 199 of SNAP25 (FIG. 2a).

Preferably, the Nop-(Z)-Pya fragment of the substrates of the invention is chosen from the following:

```
1) Nop-R-A-Pya         (SEQ ID NO: 3)
2) Nop-R-A-T-Pya       (SEQ ID NO: 4)
3) Nop-R-A-T-K-Pya     (SEQ ID NO: 5)
```

According to a preferred embodiment of the invention, the residue (Z) comprises 2 amino acids. Preferably, the Nop-(Z)-Pya sequence corresponds to the definition:

```
Nop-R-A-Pya.           (SEQ ID NO: 3)
```

A more particular subject of the invention is therefore a peptide substrate, recognized by the BoNT/A toxin, characterized in that it comprises or is constituted by the following sequence:

```
                                     (SEQ ID NO: 6)
(X)_m-S-N-K-T-R-I-D-Xaa-A-N-Nop-R-A-Pya-K-Nle-
(L)_n(GSG)_p
``` in which:
X represents an amino acid, or a chain of 2 to 52 amino acids,
m, n and p, independently of each other represent 0 or 1,
Xaa represents E or Q, i.e. any substrate as defined above comprising or constituted by the SNAP 25 (187-206) sequence in which:
the Q residue at position 197 is replaced by an Nop residue, and the T residue at position 200 is replaced by a Pya residue; the cleavage by BoNT/A of a peptide bond situated between these two amino acids Nop and Pya leads to the exaltation of fluorescence on which the invention is based,
the M residue at position 202 is replaced by an isosteric residue such as Nle,
and, if appropriate:
the E residue at position 194 is replaced by a Q residue,
and/or the L residue at position 203 is suppressed,
and/or the GSG residues at positions 204 to 206 are suppressed.

Advantageously, the N-terminal and C-terminal residues of the substrates of the invention described above and hereafter are protected, in particular by acetylation and amidification respectively, in order to avoid any non-specific degradation by aminopeptidases and/or carboxypeptidases (for example during the use of incompletely purified toxins).

A more particular subject of the invention is a substrate as defined above, characterized in that when m represents 1, X represents:
an arginine residue or a cysteine residue the thiol function of which is, if appropriate, immobilized on a solid support,
or a chain of 2 to 52 amino acids, corresponding to a fragment peptide of the protein SNAP25 (SEQ ID NO: 1) the C-terminal amino acid of which corresponds to the amino acid situated at position 186 of the sequence of the protein SNAP 25, and the N-terminal amino acid of which corresponds to one of the amino acids situated at position 135 to 185 of the sequence of the protein SNAP 25, one or more of the above-mentioned amino acids being replaced, if appropriate, by an amino acid chosen from: A, S, E, F, L, Nle.

The invention relates more particularly to a peptide substrate, recognized by BoNT/A toxin, characterized by the following sequence:

```
                                     (SEQ ID NO: 7)
Ac-(X)_m-S-N-K-T-R-I-D-Xaa1-A-N-Nop-R-A-Pya-K-Nle-
(L)_n-NH_2
``` in which:
n=0 or 1,
m=0 or 1,
X=D or C,
Xaa1 represents E or Q,
and when m=1 and X=C, the thiol function of the cysteine residue is, if appropriate, immobilized on a solid support, for example using a maleimide residue.

A more particular subject of the invention is the substrates as defined above comprising the above-mentioned SNAP 25 (187-203) sequence in which:
the Q residue at position 197 is replaced by an Nop residue, and the T residue at position 200 is replaced by a Pya residue,
the M residue at position 202 is replaced by an Nle residue,
the N-terminal S residue at position 187 is acetyl, or protected by an acetylcysteine residue,
and the C-terminal L residue at position 203 is amidified, i.e. the following sequences S1 and S2:

```
                                     (SEQ ID NO: 8)
S1: Ac-S-N-K-T-R-I-D-E-A-N-Nop-R-A-Pya-K-Nle-L-NH_2

(SEQ ID NO: 9)
S2: Ac-C-S-N-K-T-R-I-D-E-A-N-Nop-R-A-Pya-K-Nle-L-
NH_2
```

A more particular subject of the invention is substrates as defined above, corresponding to a variant of the sequences S1 and S2 in which the E194 residue is replaced by a glutamine Q residue, i.e. the following sequences S3 and S4:

```
                                     (SEQ ID NO: 10)
S3: Ac-S-N-K-T-R-I-D-Q-A-N-Nop-R-A-Pya-K-Nle-L-NH_2

(SEQ ID NO: 11)
S4: Ac-C-S-N-K-T-R-I-D-Q-A-N-Nop-R-A-Pya-K-Nle-L-
NH_2
```

A more particular subject of the invention is substrates as defined above, corresponding to a variant of the sequences S3 and S4 in which the N-terminal leucine at position 203 is suppressed, i.e. the following sequences S5 and S6:

(SEQ ID NO: 12)
S5: Ac-S-N-K-T-R-I-D-Q-A-N-Nop-R-A-Pya-K-Nle-NH$_2$ (SEQ ID NO: 13)
S6: Ac-C-S-N-K-T-R-I-D-Q-A-N-Nop-R-A-Pya-K-Nle-NH$_2$

A subject of the invention is also a substrate as defined above, characterized in that it comprises or is constituted by the above-mentioned sequence SEQ ID NO: 6 in which Xaa, n, and p are as defined above, m=1, and X represents an amino acids chain corresponding to the KAD sequence of SNAP 25 (184-186), or its derived KSD sequence.

A more particular subject of the invention is therefore a substrate as defined above, characterized in that it comprises or is constituted by the following sequence S7 (SEQ ID NO: 14):

(SEQ ID NO: 14)
S7: Ac K S D S N K T R I D E A N Nop R A Pya K Nle

L G S G NH$_2$

The speed of the enzymatic reaction of BoNT/A on its substrates is extremely dependent on the length of the substrate (V. V. Vaidyanathan et al. J. Neuro. Chem., 1999, 72, 327-337) probably because of the structure of the enzymatic sub-unit of BoNT/A (Segelke et al. Proc. Natl Acad. Sci USA, 101, 6888-6893, 2004) and of an allosteric-type mechanism (Breidenbach et al. Nature, 432, 925-929, 2004), with existence of exosites, similar to that demonstrated by the inventors for tetanic toxin (Cornille et al. J. Biol. Chem., 272, 3459-3464, 1997).

These results demonstrate that the indispensable part of SNAP 25 is constituted by the C-terminal SNAP 25 (187-203) fragment, but that the maximum affinity for the toxin is produced by the sequence preceding the 187 residue of SNAP 25 providing that it contains the sequences binding to the exosites, in particular the 156-186 or 146-186 sequences.

A subject of the present invention is therefore to propose preferred substrates of botulinum toxin type A capable of being hydrolyzed very rapidly, making it possible to detect this toxin at concentrations equal to or below the lethal dose in humans (of the order of 1 µg/70 kg). In fact, the applications of the invention are intended particularly for the detection and optionally the quantification of BoNT/A in water, different food products and air which would be infected, in particular in the case of bioterrorism. The second important application is the very precise determination of the concentrations of BoNT/A in pharmaceutical products used for different medical and aesthetic applications (Schantz and Johnson Microbiol. Rev., 1992, 56, 80-99). In the latter case, the claimed technique effectively makes it possible to assay quantitatively a concentration of the order of 10 mouse LD50 i.e. approximately 20 pg. Such low concentrations must, necessarily, be determined in pharmaceutical specialties so as to replace all the in vitro and in vivo methods existing at present.

A more particular subject of the invention is a peptide substrate selectively recognized by botulinum toxin type A, BoNT/A, characterized in that it comprises or is constituted by the above-mentioned sequence SEQ ID NO: 6 in which Xaa, n, and p are as defined above, m=1, and X represents a chain of at least 30 amino acids.

The invention relates more particularly to a substrate as defined above, characterized in that X represents a chain of at least 30 amino acids, corresponding to a peptide fragment of the protein SNAP25 the C-terminal amino acid of which corresponds to the amino acid situated at position 186 of the protein SNAP25 sequence, and the N-terminal amino acid corresponds to one of the amino acids situated at position 135 to 156 of the sequence of the protein SNAP 25 (SEQ ID NO: 1), one or more of the above-mentioned amino acids being, if appropriate, replaced by an amino acid chosen from: A, S, E, F, L, Nle.

A more particular subject of the invention is a substrate as defined above, characterized in that X represents a chain of amino acids corresponding:

to the SNAP 25 sequence (135-186), or its following derived sequences:

(SEQ ID NO: 15)
$^{135}$R R V T N D A R E N E Xaa1 D E N L E Q V S G I

I G N L R H Xaa2 A L D Xaa3 G N E I D T Q N R Q I

D R I Xaa4 E K A D$^{186}$, to the SNAP 25 sequence (141-186), or its following derived sequences:

(SEQ ID NO: 16)
$^{141}$A R E N E Xaa1 D E N L E Q V S G I I G N L R H

Xaa2 A L D Xaa3 G N E I D T Q N R Q I D R I Xaa4

E K A D$^{186}$, to the SNAP 25 sequence (146-186), or its following derived sequences:

(SEQ ID NO: 17)
$^{146}$Xaa1 D E N L E Q V S G I I G N L R H Xaa2 A L

D Xaa3 G N E I D T Q N R Q I D R I Xaa4 E K A D$^{186}$, or to the SNAP 25 sequence (156-186), or its following derived sequences:

(SEQ ID NO: 18)
$^{156}$I I G N L R H Xaa2 A L D Xaa3 G N E I D T Q N

R Q I D R I Xaa4 E K A D$^{186}$, in which Xaa1, Xaa2, Xaa3, and Xaa4, independently of each other, represent M or Nle.

The invention relates more particularly to a substrate as defined above, characterized in that it comprises or is constituted by one of the following sequences:

S8: SEQ ID NO: 19:
Ac R R V T N D A R E N E M D E N L E Q V S G I I

G N L R H M A L D M G N E I D T Q N R Q I D R I M

E K A D S N K T R I D E A N Nop R A Pya K Nle L

NH$_2$

-continued

S9: SEQ ID NO: 20:
Ac I I G N L R H M A L D M G N E I D T Q N R Q I

D R I M E K A D S N K T R I D E A N Nop R A Pya K

Nle L NH$_2$

S10: SEQ ID NO: 21:
Ac I I G N L R H Nle A L D Nle G N E I D T Q N R

Q I D R I Nle E K A D S N K T R I D E A N Nop R A

Pya K Nle L NH$_2$

A particularly preferred substrate as defined above according to the invention is that characterized in that it comprises or is constituted by the following sequence S9:

SEQ ID NO: 20:
Ac I I G N L R H M A L D M G N E I D T Q N R Q I

D R I M E K A D S N K T R I D E A N Nop R A Pya K

Nle L NH$_2$

The parameters (Km, kcat, Vmax) for the hydrolysis of S9 (see FIG. 9) prove better than those reported for SNAP 25 itself and other substrates reported to date.

The invention also relates to the non-fluorescent and fluorescent fragments, or metabolites, originating from the cleavage (FIG. 1a) of the peptide substrates of the invention by BoNT/A, the non-fluorescent metabolites being characterized in that they include the Nop residue, and the fluorescent metabolites being characterized in that they include the Pya residue.

A more particular subject of the invention is the above-mentioned fluorescent metabolites originating from the cleavage of the peptide substrates of the invention by BoNT/A at the level of the Nop$^{197}$-$^{198}$R bond, i.e. the metabolites of formula:

R-A-Pya-K-Nle-(L)$_n$(GSG)$_p$-NH$_2$     (SEQ ID NO: 22)

in which n and p are as defined above, and more particularly:

the following fluorescent metabolite M1, originating in particular from the cleavage of the substrates S1, S2, S3, S4, S8, S9, and S10 by BoNT/A at the level of the Nop$^{197}$-$^{198}$R bond, M1: R-A-Pya-K-Nle-L-NH$_2$     (SEQ ID NO: 23)

the following fluorescent metabolite M2, originating in particular from the cleavage of the substrates S5 and S6 by BoNT/A at the level of the Nop$^{197}$-$^{198}$R bond, M2: R-A-Pya-K-Nle-NH$_2$.     (SEQ ID NO: 24)

the following fluorescent metabolite M3, originating in particular from the cleavage of the substrate S7 by BoNT/A at the level of the Nop$^{197}$-$^{198}$R bond, M3: R-A-Pya-K-Nle-L-G-S-G-NH$_2$.     (SEQ ID NO: 25)

The substrates according to the present invention are useful in several ways:
  they make it possible to rapidly detect within a liquid or substance the possible presence of botulinum toxin type A, at concentrations below the lethal dose in humans,
  they have a very high selectivity vis-à-vis the other botulinum toxins, and other peptidases,
  they make possible high-throughput screening of potential inhibitors of type A botulinum toxin,
  they give rise to only two metabolites due to the selective cleavage of the Nop-R bond by BoNT/A.

Consequently, the present invention relates to the use of a substrate as defined previously for the implementation of methods for the detection, identification and/or assay of BoNT/A or of a compound capable of inhibiting or activating BoNT/A, and for the implementation of in vitro methods for diagnosing the presence of BoNT/A in a sample obtained from various media such as water, air, milk, drink, food, and biological media such as blood, urine, and cerebrospinal fluid, as well as for the precise determination of BoNT/A concentrations during the production, purification, and conditioning of pharmaceutical compositions for the purposes of therapeutic use in humans or animals (in particular within the framework of neurological pathologies), or cosmetic compositions.

According to a preferred variant of the invention, the substrates are used to search for BoNT/A inhibitors and quantify their inhibiting power.

A subject of the present invention is also a method for detecting, identifying and/or assaying a compound capable of inhibiting BoNT/A characterized in that it comprises:
  bringing together a substrate according to the invention in solution with said BoNT/A or its light chain (as described in particular in Cai and Singh, Biochemistry (2001) 40, 4693-4702), and at least one compound capable of inhibiting BoNT/A;
  measuring the fluorescence, emitted by the above-mentioned fluorescent metabolites formed during the preceding stage of hydrolysis of the substrate, in the presence and/or in the absence of said compound, a diminution of fluorescence between the measurement carried out in the presence of this compound and that carried out in the absence of this compound, then indicating that the tested compound is an inhibitor of BoNT/A.

The addition of increasing doses of a compound capable of inhibiting the enzymatic activity of BoNT/A vis-à-vis a substrate according to the present invention, finds expression in a diminution of the intensity of the fluorescence due to the diminution of the quantity of metabolite formed by BoNT/A. The measurement of this intensity in relation to a standard curve established by mixture of the substrate and the fluorescent metabolite formed, therefore makes it possible to evaluate the inhibiting power as a percentage of inhibition at a given fixed concentration of inhibiting compound, or to precisely determine its IC50 then its Ki using the Km of the substrate and several concentrations of the inhibiting product.

A compound to which the test defined above is applied in order to determine its inhibiting activity vis-à-vis BoNT/A can be various in nature, without limitation and can be presented in an isolated form, be known or unknown and/or be present in a bank of compounds, a biological extract.

The extreme sensitivity of the assay makes it possible to operate in very small volumes (50 or 100 µl) with concentrations of the order of 5 to 50 µM of the chosen substrate (in particular S5, S8 and S9). The test can therefore be used in plates with 96 wells or more, allowing its automation with automatic determination of Ki when the reading fluorimeter is connected to a computer possessing appropriate commercial software.

The present invention therefore proposes a test for identification of BoNT/A inhibitors as well as the determination of their inhibiting powers by a very rapid fluorimetric test, which is reproducible, allowing tests that can be automated and carried out in very large numbers, and which can be adapted to a high-throughput selection of inhibiting molecules.

The present invention also proposes the production of new industrial products, which can optionally be used in the form of kits, in particular comprising ready-to-use 96, 192 and 384-well plates, and containing a substrate as defined above according to the invention and the reagents necessary for determination of the BoNT/A inhibiting or activating powers. The present invention moreover proposes kits comprising tablets containing together one of the substrates of the invention (in particular S9) and the reagents necessary for the development of the enzymatic reaction and therefore for the appearance of intense fluorescence in the case of the addition of water or of a substance containing BoNT/A. In this case, the kits of the invention advantageously also include a fluorimeter, the emission wavelength of which is preferably comprised between 360 and 420 nm, and the excitation wavelength is comprised between 320 and 350 nm as well as the reagents EDTA and/or separate or associated gangliosides and any substances capable of inhibiting enzymes other than BoNT/A without affecting the activity of the latter.

Another aspect of the invention relates to an in vitro method for diagnosing the presence of BoNT/A in a sample as defined above, or measuring the concentrations of BoNT/A during the stages of production, purification, and conditioning of pharmaceutical or cosmetic compositions in a sample taken during these stages.

The invention also relates to an in vitro method for diagnosing the presence of BoNT/A in the human or animal organism, using a substrate according to the invention.

Such diagnosis or measurement methods include:
- a stage of bringing together a substrate according to the invention in solution with a sample as defined above (for example samples taken from foods, liquids, or human blood samples, optionally contaminated by BoNT/A);
- measurement of the fluorescence emitted by any above-mentioned fluorescent metabolites formed during the preceding stage, giving evidence of the presence of BoNT/A in said sample, which can be quantified using appropriate standard curves (see attached figures),
- if appropriate and for the purpose of removing falsely positive responses, the elimination of the fluorescence emitted during the above-mentioned stage by the addition of a zinc chelating agent, such as for example, and in non-limiting manner, ethylene diamine tetracetate EDTA which inhibits the metalloprotease activity of BoNT/A (FIG. 3), or by the addition of gangliosides, which block the latter by the formation of an inactive complex.

The attached figures and examples are presented by way of illustration, without limiting the present invention.

FIGURES

FIG. 1: Difference in exaltation of fluorescence during cleavage by BoNT/A of the substrate 1 (peptide 1), Ac-S-N-K-T-R-I-D-E-AN-Pya-R-A-Nop-K-Nle-L-NH$_2$ (SEQ ID NO: 27) (■, bottom graph) and 2 (peptide 2), Ac-S-N-K-T-R-I-D-E-A-N-Nop-R-A-Pya-K-Nle-L-NH$_2$ (SEQ ID NO: 8) (♦, top curve). The time in minutes is represented along the x-axis, and the fluorescence (U.A.) along the y-axis.

FIG. 2: a) Diagram of the cleavage of the substrates according to the invention by BoNT/A.
b) Comparison of the emission of fluorescence of the substrate S1 ($10^{-5}$M) and its metabolite M1 (at 5 $10^{-7}$M corresponding to 5% degradation). Excitation at 343 nm. The wavelength in nm is indicated along the x-axis and the intensity emitted along the y-axis.

Figure 3:
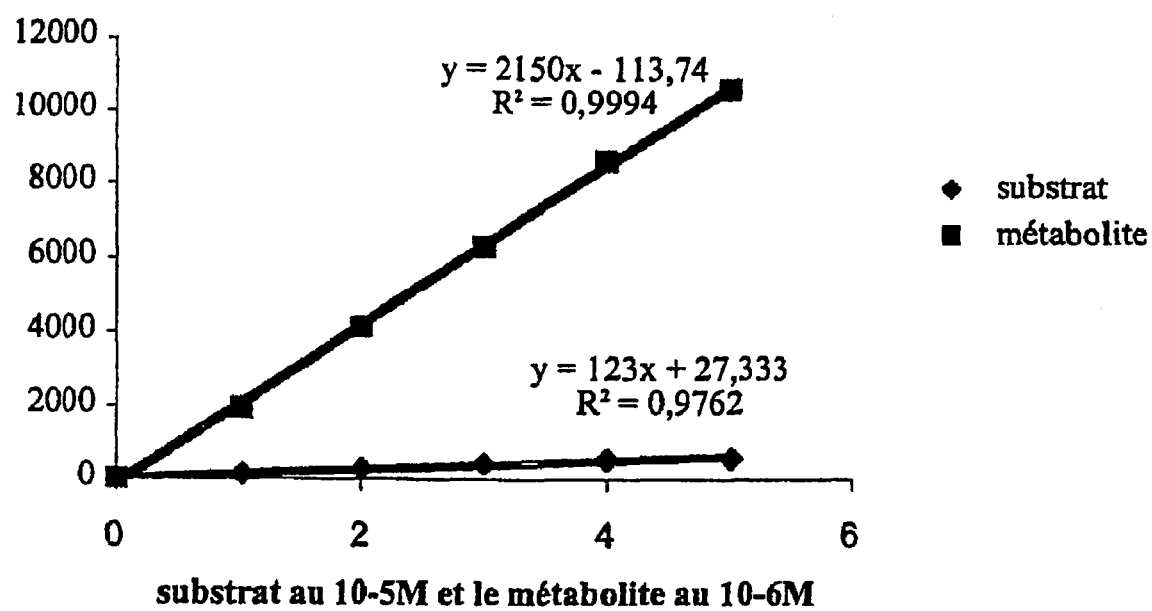

FIG. 3: Standard curve of fluorescence for the determination of the % of substrate degraded during an assay.

FIG. 4: Fluorescence emitted by the degradation of the substrate S1 (50 µM) in 1 hour by BoNT/A and inhibition of the fluorescence (therefore of the enzymatic activity by EDTA).

FIG. 5: Fluorimetric BoNT/A quantification test with the substrate S9. The concentrations are expressed in mouse LD50, i.e. 1 LD50=2 pg. The time in minutes is indicated along the x-axis, and the fluorescence (U.A.) along the y-axis.

Figure 6:
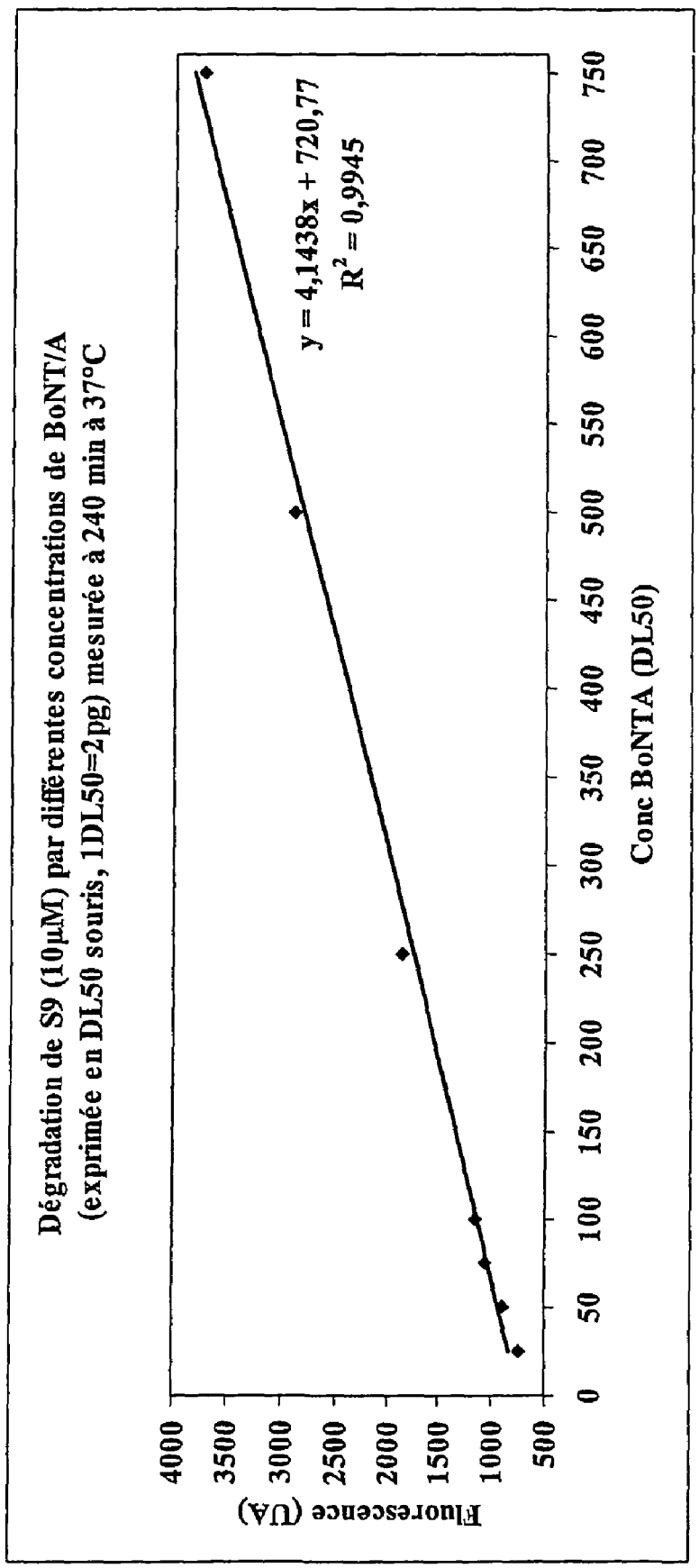

FIG. 6: Linear relation between exaltation of fluorescence (along the y-axis, U.A.) and concentration of BoNT/A (along the x-axis, in LD50) at a time determined with the substrate S9.

Figure 7:
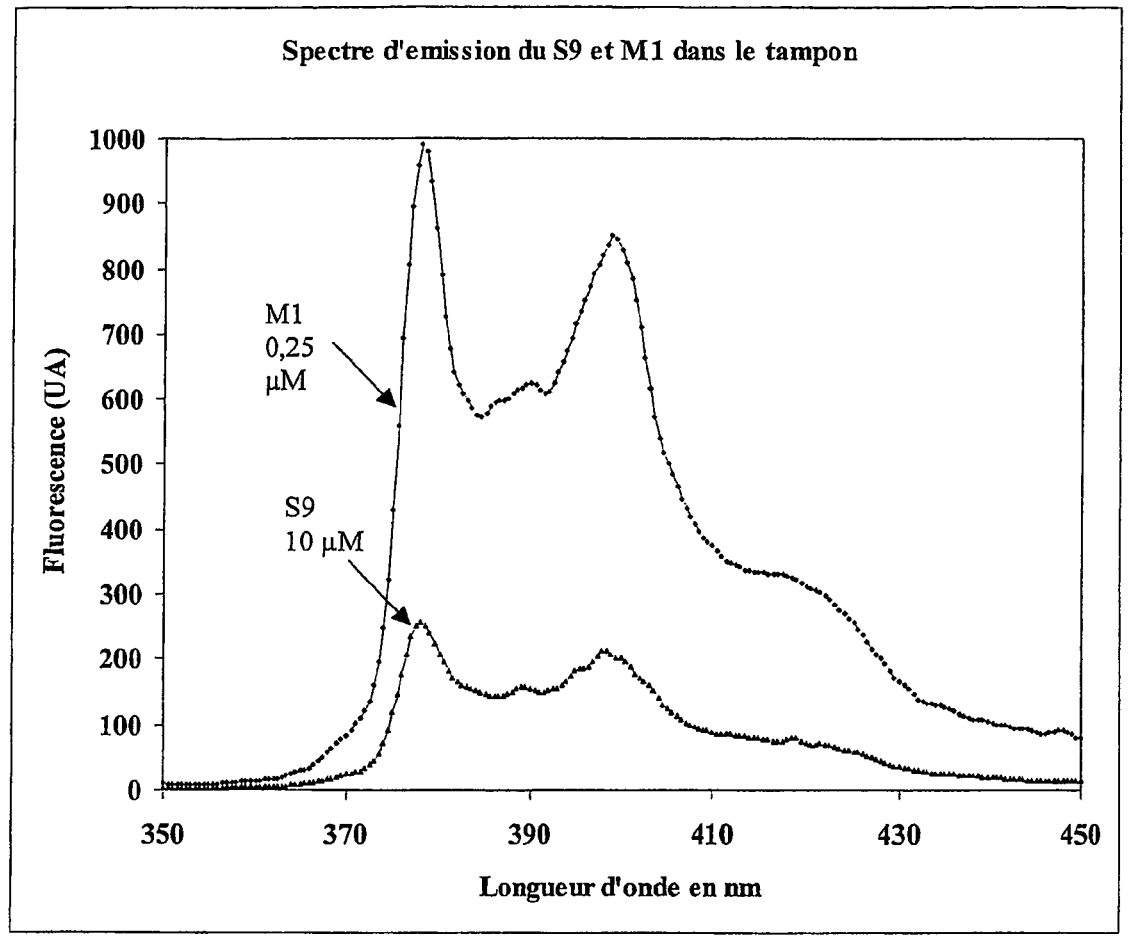

FIG. 7: Emission of fluorescence of the substrate S9 and its metabolite M1 corresponding to 2.5% degradation; excitation at 343 nm. The wavelength in nm is indicated along the x-axis, and the fluorescence in U.A. along the y-axis.

FIG. 8: Analytical parameters of S9 (SEQ ID NO: 20).

FIG. 9: Kinetic parameters of the degradation of S9 by BoNT/A. The Km and the catalytic constants prove to be more favorable than for SNAP 25. The PL50 concentration is indicated in µM along the x-axis and the speed of cleavage (in pmol/min/µg) along the y-axis. Insert: ratio of speed/concentration of the substrate in pmol/min/µg of enzyme/µM of substrate along the x-axis and speed in pmol/min/µg along the y-axis.

EXAMPLES

1) Synthesis of the Peptides

The claimed compounds can be obtained by the usual methods of synthesis in solid phase according to Merrifield's method on an automatic synthetizer such as for example Applied Biosystems' device 431A. The chemistry used corresponds to Fmoc technology. The deprotection of the side chains and the cleavage of the peptidyl resin are carried out by trifluoroacetic acid as described by E. Atherton and R. C. Sheppard (1989) in "Solid phase peptides synthesis: a practical approach, IRL Press, Oxford". The couplings are carried out according to the conventional techniques using coupling agents such as HATU, Bop, PyBrop and preferably using dicyclohexylcarbodiimide (DCC) in the presence of hydroxybenzotriazole (HOBT). Details of the techniques used can be found in the publications reporting synthesis of very large peptides carried out by the inventors (Cornille F. et al., J. Pept. Res., 1999, 54, 427-435; Cornille F. et al., Nucleic Ac. Res., 1998, 26, 2143-2149; Cornille F. et al., Int. J. Pept. Rot. Res., 1990, 36, 551-558; de Rocquigny H. et al., Proc. Natl. Acad. Sci., 1992, 89, 6472-6476). L-pyrenylalanine is obtained according to an asymmetrical synthesis method described in the publication by Soleilhac et al. (Anal. Biochem., 1996, 241, 120-127). The peptides are purified by semi-preparative HPLC. The purity of the peptides is estimated as greater than 95% by reversed phase HPLC and their identification is obtained by mass spectrometry.

3) Fluorimetric BoNT/A Detection Test

The substrate (S1 for example) is incubated, 50 μM for 1 hour with an unknown quantity of double-chain BoNT/A at 37° C. in 100 ml of 20 mM Hepes buffer, pH 7.4, containing BSA (1 mg/ml), ZnSO4 (0.3 mM) and DTT (5 mM). The

```
Substrate S1:
Ac-S-N-K-T-R-I-D-E-A-N-Nop-R-A-Pya-K-Nle-L-NH2:              (SEQ ID NO: 8)
M (theo) 2233.53; MH+ (exp) 2234.20

Substrate S2:
Ac-C-S-N-K-T-R-I-D-E-A-N-Nop-R-A-Pya-K-Nle-L-NH2:            (SEQ ID NO: 9)
M (theo) 2336.67; MH+ (exp) 2337.98

Substrate S3:
Ac-S-N-K-T-R-I-D-Q-A-N-Nop-R-A-Pya-K-Nle-L-NH2:              (SEQ ID NO: 10)
M (theo) 2232.55; MH+ (exp) 2233.78

Substrate S4:
Ac-C-S-N-K-T-R-I-D-Q-A-N-Nop-R-A-Pya-K-Nle-L-NH2:            (SEQ ID NO: 11)
M (theo) 2335.69; MH+ (exp) 2336.48

Substrate S5:
Ac-S-N-K-T-R-I-D-Q-A-N-Nop-R-A-Pya-K-Nle-NH2:                (SEQ ID NO: 12)
M (theo) 2119.39; MH+ (exp) 2120.54

Substrate S6:
Ac-C-S-N-K-T-R-I-D-Q-A-N-Nop-R-A-Pya-K-Nle-NH2:              (SEQ ID NO: 13)
M (theo) 2222.53; MH+ (exp) 2223.80

Metabolite M1:
R-A-Pya-K-Nle-L-NH2                                          (SEQ ID NO: 23)
M (theo) 867.12; MH+ (exp) 868.24

Metabolite M2:
R-A-Pya-K-Nle-NH2.                                           (SEQ ID NO: 24)
M(theo) 756.96; MH+ (exp) 758.02

Substrate S7:
Ac K S D S N K T R I D E A N Nop R A Pya K Nle L G S G NH2:  (SEQ ID NO: 14)
M(theo): 2764.81; M(exp): 2764.0

Substrate S9:
Ac I I G N L R H M A L D M G N E I D T Q N R Q I D R I M E K A D   (SEQ ID NO: 20)

S N K T R I D E A N Nop R A Pya K Nle-L NH2:
M(theo): 5827.7; M (exp): 5826.9

Substrate S10:
Ac I I G N L R H Nle A L D Nle G N E I D T Q N R Q I D R I Nle E K  (SEQ ID NO: 21)

A D S N K T R I D E A N Nop R A Pya K Nl L NH2:
M (theo): 5773.58; M (exp): 5773.2
```

2) Physico-Chemical Characteristics of the Substrate S9

Amino Acid Analysis

| Asx: 9.76/10 | Thr: 1.91/2 | Cys: X |
| Glx: 5.03/5 | Ala: 4.17/4 | Ile: 5.14/6 |
| Ser: 1.00/1 | Pro: X | Leu: 4.20/3 |
| Gly: 1.97/2 | Tyr: X | Phe: X |
| His: 0.96/1 | Val: X | Trp: X |
| Arg: 5.07/5 | Met: 2.58/3 | Lys: 3.14/3 | pNO2-Phe was detected but not quantified. Nle co-elutes with Leu. There is incomplete hydrolysis between Ile-Ile. Met is partially destroyed during the hydrolysis (see also HPLC of S9, FIG. 8).

enzymatic hydrolysis is stopped by placing the sample at 4° C., or adding 5 μL of 2N HCl, and the fluorescence emitted is directly read with the fluorimeter ($\lambda$ex 343 nm, $\lambda$em 377 nm).

The measured intensity of fluorescence is related to a standard curve in order to establish the quantity of BoNT/A present in the sample. The experiments carried out with several quantities of BoNT/A show that the precision reaches ±10% of the quantity of neurotoxin in the range 0.2 ng/ml to 15 ng/ml (see FIG. 5).

4) Fluorimetric BoNTA Detection Test with the Substrate S9 (FIG. 5)

The substrate S9 is incubated, 10 μM as a function of time with different concentrations of double-chain BoNT/A (1 mouse LD50=2 pg) at 37° C. in 100 μL of 20 mM Hepes buffer, pH 7.4, containing BSA (1 mg/ml), ZnSO$_4$ (0.3 mM) and DTT (5 mM). The fluorescence emitted is read directly with a cytofluor device ($\lambda$ex 340 nm, $\lambda$em 400 nm). Its increase with respect to the control is directly linked to the BoNTA concentration every time. This therefore makes it possible to determine the quantity of toxin in a sample with an unknown BoNTA concentration (see FIG. 6). With S9 a BoNT/A concentration of 0.2 ng/ml can be quantified.

These experiments can be carried out with different types of fluorimeter and variable sample volumes for example from 50 μl to 2 ml.

5) Determination of the Cleavage Site of S9 (10 μM) by BoNTA (50 ng/100 μl)

The analysis was carried out in parallel by LC-MS (Kromasil C18 CH$_3$CN/H$_{20}$ (0.5% TFA) gradient 10% CH3CN to 90% in 60 minutes; electrospray mass on LCD (Avantage Thermo Finnigan) and HPLC (Kromasil C18 CH$_3$CN/H$_{20}$ (0.5% TFA) gradient 10% CH3CN to 90% in 30 minutes.

The fluorescent metabolite M1 is detected with an m/z=870.1 corresponding to M+H.

Metabolite M1: R A Pya K Nle-L NH$_2$ (SEQ ID NO: 23)

The non-fluorescent metabolite M3 is detected with m/z=4975.0 corresponding to (M+H)

```
Metabolite M4:                              (SEQ ID NO: 26)
Ac I I G N L R H M A L D M G N E I D T Q N R Q I
D R I M E K A D S N K T R I D E A N Nop
```

It has also been verified by HPLC (co-injection with the metabolites synthesized) that there are only two metabolites formed.

6) Comparison of Fluorescence Induced by the Action of Botulinum Toxin Type A on the Following Repressed Fluorescence Substrates (FIG. 1)

```
Peptide 1:                                   (SEQ ID NO: 27)
Ac-S-N-K-T-R-I-D-E-A-N-Pya-R-A-Nop-K-Nle-L-NH₂

Peptide 2:                                   (SEQ ID NO: 8)
Ac-S-N-K-T-R-I-D-E-A-N-Nop-R-A-Pya-K-Nle-L-NH₂
```

The experiment (see FIG. 1) shows the very clear superiority of the arrangement Nop-Z-Pya relative to Pya-Z-Nop. The latter produces a much smaller variation in fluorescence in order to meet the requirements of the present patent (precise assay of BoNT/A in pharmaceutical preparations, detection of very small doses of BoNT/A capable of producing toxic effects in humans in various preparations, in particular water.

---

The invention claimed is:
1. A peptide substrate selectively recognized by botulinum toxin type A (BoNT/A) comprising in its peptide structure a Nop-(Z)-Pya fragment in which Z represents an amino acid chain, said fragment being cleaved by BoNT/A, wherein the Nop-(Z)-Pya fragment is chosen from the following:

1) Nop-R-A-Pya,        (SEQ ID NO: 3)
    2) Nop-R-A-T-Pya, and  (SEQ ID NO: 4)
    3) Nop-R-A-T-K-Pya.    (SEQ ID NO: 5)

2. The peptide substrate according to claim 1, wherein the Nop-(Z)-Pya fragment corresponds to the Nop-R-A-Pya sequence (SEQ ID NO:3).

3. The peptide substrate according to claim 1, comprising the following sequence:

(SEQ ID NO: 6)
Ac-(X)$_m$-S-N-K-T-R-I-D-Xaa-A-N-Nop-R-A-Pya-K-Nle-(L)$_n$(GSG)$_p$-NH$_2$, in which:
X represents an amino acid, or a chain of 2 to 52 amino acids,
m, n and p, independently of each other represent 0 or 1, and
Xaa represents E or Q.

4. The peptide substrate according to claim 1, comprising the following sequence:

(SEQ ID NO: 6)
Ac-(X)$_m$-S-N-K-T-R-I-D-Xaa-A-N-Nop-R-A-Pya-K-Nle-(L)$_n$(GSG)$_p$-NH$_2$ in which:
X represents an amino acid, or a chain of 2 to 52 amino acids,
m, n and p, independently of each other represent 0 or 1, and
Xaa represents E or Q,
wherein when m represents 1, X represents:
an arginine residue or a cysteine residue the thiol function of which is, if appropriate, immobilized on a solid support, or
a chain of 2 to 52 amino acids, corresponding to a peptide fragment of the protein SNAP 25, the C-terminal amino acid of which corresponds to the amino acid situated at position 186 of the sequence of the protein SNAP 25 corresponding to SEQ ID NO: 1, and the N-terminal amino acid of which corresponds to one of the amino acids situated at position 135 to 185 of the sequence of the protein SNAP 25 corresponding to SEQ ID NO: 1.

5. The peptide substrate according to claim 1, comprising at least one of the following sequences S1 to S6:

S1:
(SEQ ID NO: 8)
Ac-S-N-K-T-R-I-D-E-A-N-Nop-R-A-Pya-K-Nle-L-NH$_2$;

S2:
(SEQ ID NO: 9)
Ac-C-S-N-K-T-R-I-D-E-A-N-Nop-R-A-Pya-K-Nle-L-NH$_2$;

S3:
(SEQ ID NO: 10)
Ac-S-N-K-T-R-I-D-Q-A-N-Nop-R-A-Pya-K-Nle-L-NH$_2$;

S4:
(SEQ ID NO: 11)
Ac-C-S-N-K-T-R-I-D-Q-A-N-Nop-R-A-Pya-K-Nle-L-NH$_2$;

S5:
(SEQ ID NO: 12)
Ac-S-N-K-T-R-I-D-Q-A-N-Nop-R-A-Pya-K-Nle-NH$_2$; and

S6:
(SEQ ID NO: 13)
Ac-C-S-N-K-T-R-I-D-Q-A-N-Nop-R-A-Pya-K-Nle-NH$_2$.

6. The peptide substrate according to claim 1, comprising the following sequence:

(SEQ ID NO: 6)
Ac-(X)$_m$-S-N-K-T-R-I-D-Xaa-A-N-Nop-R-A-Pya-K-Nle-(L)$_n$(GSG)$_p$-NH$_2$ in which:
X represents an amino acid chain corresponding to the KAD sequence of SNAP 25 (184-186), or its derived KSD sequence,
m, n and p, independently of each other represent 0 or 1, and
Xaa represents E or Q.

7. The peptide substrate according to claim 6, comprising the following sequence S7:

(SEQ ID NO: 14)
S7: Ac K S D S N K T R I D E A N Nop R A Pya K Nle L G S G NH$_2$.

8. The peptide substrate according to claim 1, comprising the following sequence:

(SEQ ID NO: 6)
Ac-(X)$_m$-S-N-K-T-R-I-D-Xaa-A-N-Nop-R-A-Pya-K-Nle-(L)$_n$(GSG)$_p$-NH$_2$ in which:
X represents an amino acids chain of at least 30 amino acids,
m, n and p, independently of each other represent 0 or 1, and
Xaa represents E or Q.

9. The peptide substrate according to claim 8, wherein X represents an amino acid chain corresponding to:
the SNAP 25 (135-186) sequence (SEQ ID NO: 1), or the following derived sequence:

(SEQ ID NO: 15)
$^{135}$R R V T N D A R E N E Xaa1 D E N L E Q V S G I I G N L R H Xaa2 A L D Xaa3 G N E I D T Q N R Q I D R I Xaa4 E K A D$^{186}$, the SNAP 25 (141-186) sequence (SEQ ID NO: 1), or the following derived sequence:

```
                                                   (SEQ ID NO: 16)
¹⁴¹A R E N E Xaa1 D E N L E Q V S G I I G N L R H

Xaa2 A L D Xaa3 G N E I D T Q N R Q I D R I Xaa4

E K A D¹⁸⁶,
``` the SNAP 25 (146-186) sequence (SEQ ID NO: 1), or the following derived sequence:

```
                                                   (SEQ ID NO: 17)
¹⁴⁶Xaa1 D E N L E Q V S G I I G N L R H Xaa2 A L D

Xaa3 G N E I D T Q N R Q I D R I Xaa4 E K A D¹⁸⁶,
``` or the SNAP 25 (156-186) sequence (SEQ ID NO: 1), or the following derived sequence:

```
                                                   (SEQ ID NO: 18)
¹⁵⁶I I G N L R H Xaa2 A L D Xaa3 G N E I D T Q N R

Q I D R I Xaa4 E K A D¹⁸⁶,
``` wherein Xaa1, Xaa2, Xaa3, and Xaa4, independently of each other, represent M or Nle.

10. The peptide substrate according to claim 8, comprising at least one of the following sequences S8 to S10:

```
S8:                                                (SEQ ID NO: 19)
Ac R R V T N D A R E N E M D E N L E Q V S G I I G

N L R H M A L D M G N E I D T Q N R Q I D R I M E

K A D S N K T R I D E A N Nop R A Pya K Nle L NH₂;
```

```
S9:                                                (SEQ ID NO: 20)
Ac I I G N L R H M A L D M G N E I D T Q N R Q I D

R I M E K A D S N K T R I D E A N Nop R A Pya K

Nle L NH₂; and
```

```
S10:                                               (SEQ ID NO: 21)
Ac I I G N L R H Nle A L D Nle G N E I D T Q N R Q

I D R I Nle E K A D S N K T R I D E A N Nop R A

Pya K Nle L NH₂.
```

11. The peptide substrate according to claim 8, comprising the following sequence S9

```
                                                   (SEQ ID NO: 20)
Ac I I G N L R H M A L D M G N E I D T Q N R Q I

D R I M E K A D S N K T R I D E A N Nop R A Pya K

Nle L NH₂.
```

12. A kit, comprising a peptide substrate according to claim 1 and BoNT/A.

13. The kit according to claim 12, further comprising a fluorimeter.

14. The kit according to claim 12, further comprising EDTA, separate or associated gangliosides, and/or a substance capable of inhibiting enzymes other than BoNT/A without affecting the enzyme activity of BoNT/A.

* * * * *